Figure 1:
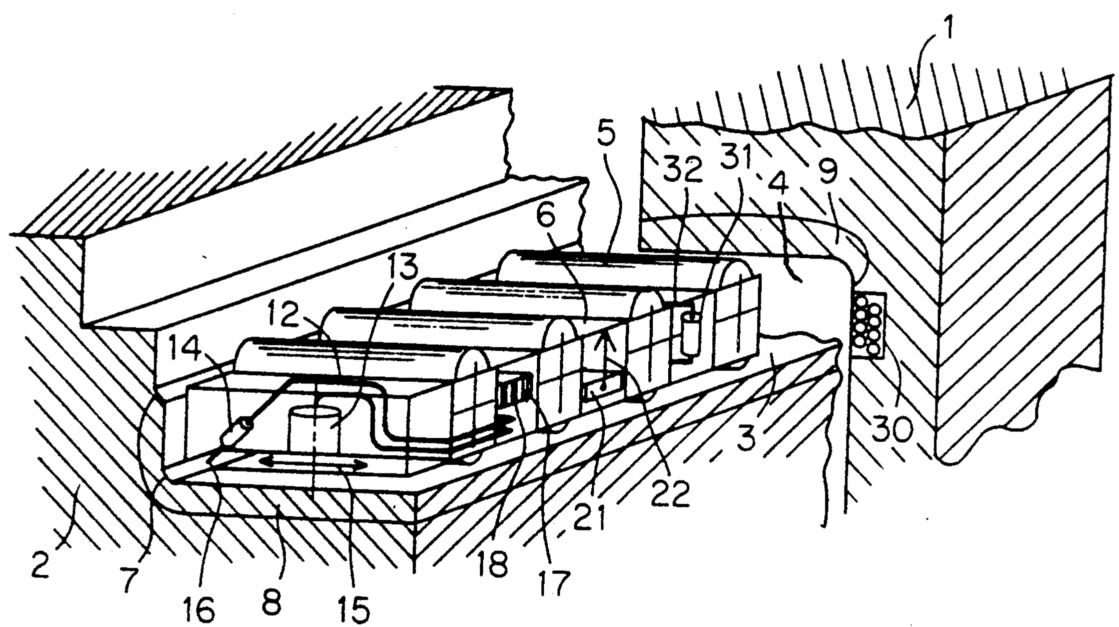

US005226736A

United States Patent [19]

Becker et al.

[11] Patent Number: 5,226,736

[45] Date of Patent: Jul. 13, 1993

[54] DEVICE FOR MONITORING ANTIFRICTION BEARINGS

[75] Inventors: Dieter Becker, Lippstadt; Engelbert Koss, Wadersloh-Liesborn; Wolfgang Werther, Lippstadt-Rixbeck; Johannes Wozniak, Lippstadt-Lipperode, all of Fed. Rep. of Germany

[73] Assignee: Hoesch AG, Dortmund, Fed. Rep. of Germany

[21] Appl. No.: 927,111

[22] Filed: Aug. 7, 1992

[30] Foreign Application Priority Data

Aug. 30, 1991 [DE] Fed. Rep. of Germany ....... 4128807

[51] Int. Cl.[5] .............................................. F16C 19/30

[52] U.S. Cl. ..................................... 384/448; 384/624

[58] Field of Search ............... 384/448, 624, 618, 548, 384/456, 619

[56] References Cited

U.S. PATENT DOCUMENTS

| | | | |
|---|---|---|---|
| 4,063,786 | 12/1977 | Rall | 384/624 |
| 4,641,978 | 2/1987 | Kapich | 384/624 |
| 5,017,866 | 5/1991 | Santos et al. | 384/448 |
| 5,085,519 | 2/1992 | Dougherty | 384/448 |

*Primary Examiner*—Lenard A. Footland
*Attorney, Agent, or Firm*—Max Fogiel

[57] ABSTRACT

A device for detecting and monitoring damage to races (3 and receiver 24) or adjacent areas on the rings (1 and 2) in antifriction bearings. The object of the present invention is a device that will not only precisely measure the dimensions of cracks and pits in the race or in the transition between the races and the ring but will also forward the results to the processing equipment with no perforations in the ring and without cables and plugs. One or more sensors (13 and 14) are positioned between the rolling components (5) inside the antifriction bearing, whereby the signals they generate are transmitted electromagnetically to a receiver antenna (23) outside the antifriction bearing.

8 Claims, 3 Drawing Sheets

1 5 32 31 4 9 6 13 12 14 30 3 22 21 2 7 16 8 15 18 17

DEVICE FOR MONITORING ANTIFRICTION BEARINGS

DESCRIPTION

The invention concerns a device for monitoring antifriction bearings.

In various applications, especially with respect to the large-scale antifriction bearings employed off shore with cranes and buoys, it is sensible to provide testing devices to detect defects and cracks in the race or in adjacent areas of the ring without destroying or disassembling the bearing.

German 2 418 056 A1 proposes for this purpose measuring the displacement between the outer ring and the inner ring. Such displacement occurs when the race or rolling components become worn. The extent of displacement is a measure of the level of destruction of the race or rolling component. Cracks in the race or in the transition between the race and the ring cannot be detected by this method. EP 0 228 731 A1 accordingly proposes introducing an opening in at least one ring to accommodate an ultrasonic probe. Material failure in the other ring will be detected through an interface on it. One drawback to this design is that superficial defects can be measured only indirectly, meaning that the head of the ultrasonic detector interfacing with the interface must emit radiation through part of the ring in order to detect superficial defects in the exposed area of the race system, and inclusions or alterations in the structure of the material can contaminate the results. Again, the field of measurement is too restricted to precisely determine how deep any cracks are. Still another drawback is that all known monitoring systems necessitate electric connections extending out from the sensors or probes and through breaches in the ring to the processing equipment by way of plugs. When the bearings, especially large-scale bearings, are employed off shore in buoys, which are partly submerged, such a design is often difficult to use because of the frequency of short circuits and the difficulty of reaching the rings.

The object of the present invention is a device for detecting and monitoring damage to the races in antifriction bearings that will not only precisely measure the dimensions of cracks and pits in the race or in the transition between the races and the ring but will also forward the results to the processing equipment with no perforations in the ring and without cables and plugs.

This object is attained in accordance with the invention. The advantage of the invention is that the monitoring device occupies no additional space in the antifriction bearing. The device can also be operated independent of the location of and environment around the bearing. No specially designed access to the bearing system is necessary. The life of an embodiment is in no way limited because of the monitoring device's power demands. One advantage over the previously employed ultrasonic sensors is the continuous monitoring provided by the high-frequency electromagnetic coils recited. These sensors, in contrast to ultrasonic sensors, do not rest against the ring being tested and are accordingly not affected by wear from grinding processes.

Figure 2:
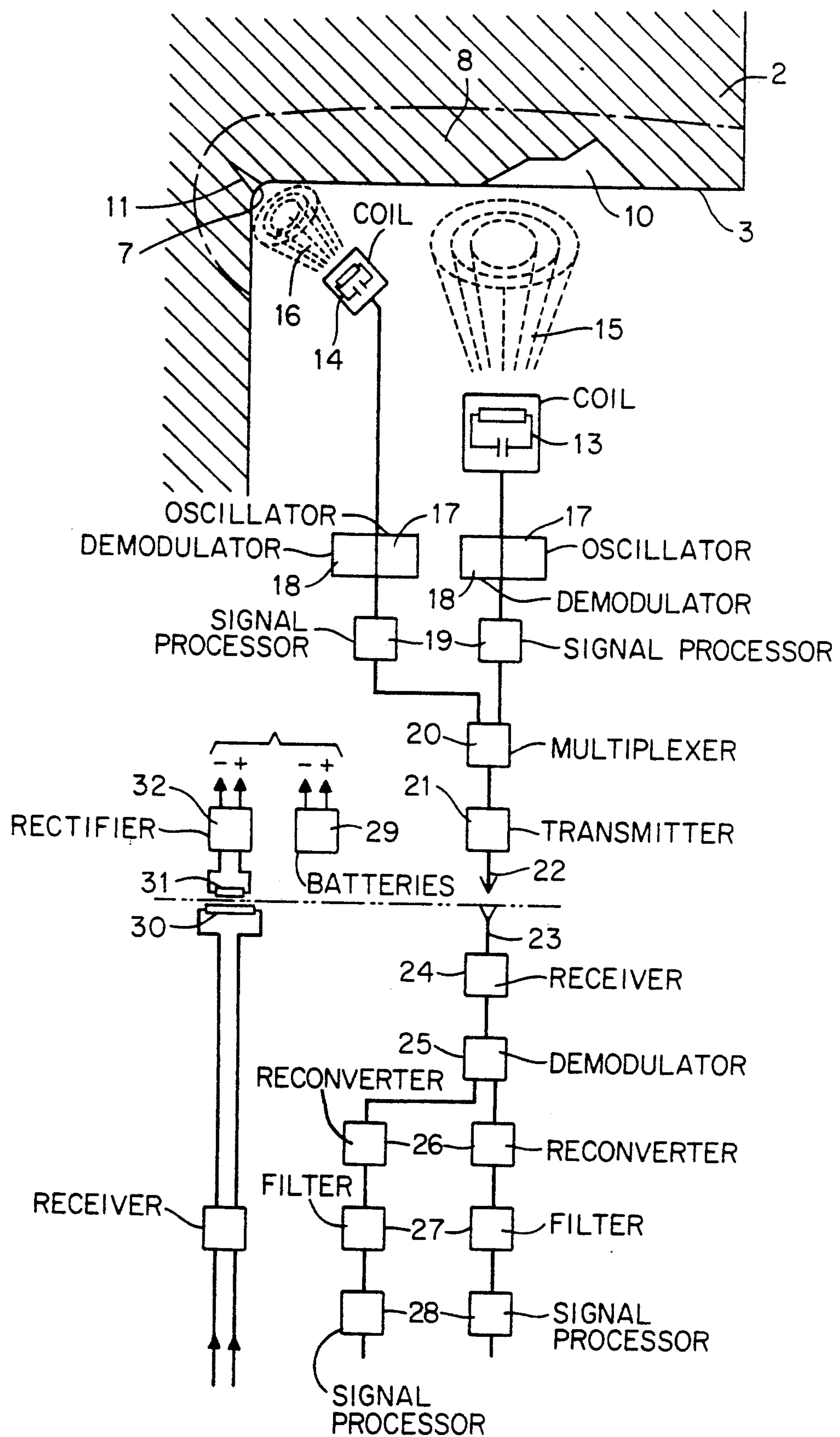
Figure 3:
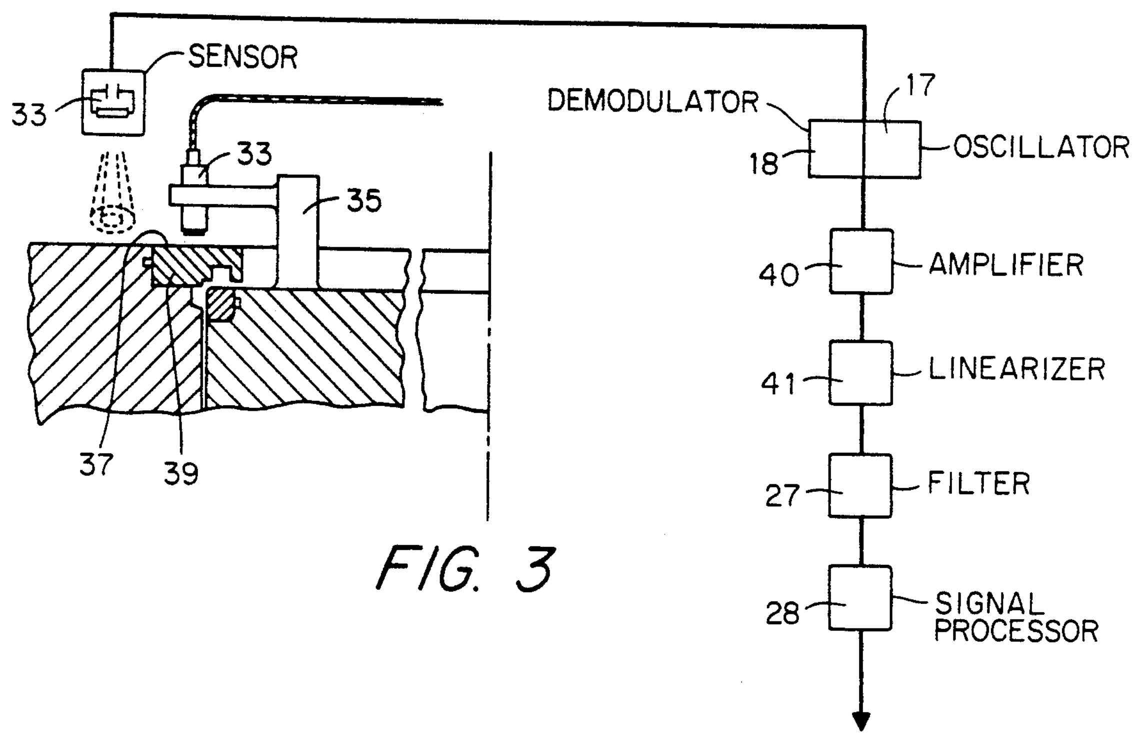
Figure 4:
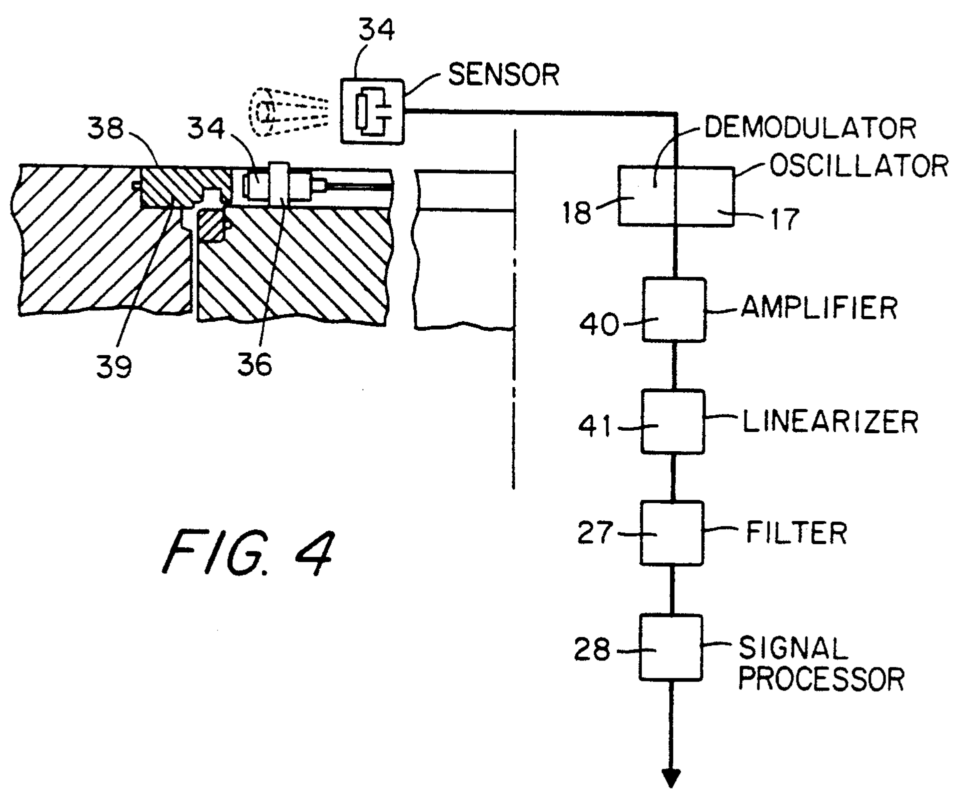

One embodiment of the invention will now be specified with reference to the drawing, wherein FIG. 1 illustrates an instrumentation system operating in conjunction with the bearing components that surround it, FIG. 2 the systems design of such an instrumentation system employing high-frequency electromagnetic coils as sensors, FIG. 3 the design of an inductive distance sensor that detects the axial mutual displacement of the rings, and FIG. 4 the system illustrated in FIG. 3 as employed to detect radial displacement.

A large-scale antifriction bearing comprises an outer ring 1 and an inner ring 2 with rolling components 5 secured between them and traveling over races 3 and 4. The rolling components 5 in the illustrated embodiment are cylindrical rollers. They are positioned and separated by a cage 6, which has webs 12 extending between the rolling components 5. Races 3 and 4 and to some extent the transition 7 between race 3 and inner ring 2 have been heat treated to create hardness coatings 8 and 9. Two high-frequency electromagnetic coils 13 and 14 are positioned in one or more webs 12 to detect pits 10 in race 3 or cracks 11 in the transition 7 between race and ring. The high-frequency electromagnetic fields 15 and 16 within the coils' range of activity generate turbulence in the upright plane of race 3 or transition 7. The resulting magnetic coupling attenuates the oscillating circuit in accordance with the dimension of the air gap. The resulting change in amplitude dictates the magnitude of the signal.

FIG. 2 illustrates how the signals are processed. The components involved are an oscillator 17, a demodulator 18, a signal processor 19, a multiplexer 20, a transmitter 21, a transmitter antenna 22, a receiver antenna 23, a receiver 24, a demodulator 25, a reconverter 26, a filter 27, and a signal processor 28. These components can also be accommodated, either separate or integrated, in additional webs 12 in cage 6. Coils 13 and 14 and their associated electronics, including the transmitter, can be operated in their capacity as sensors by batteries 29. It is in this event reasonable to provide means of engaging and disengaging them with electric signals.

Power is supplied inductively to the illustrated embodiment from outside. An induction coil 30 is for this purpose positioned in outer ring 1 inside the antifriction bearing. The power supplied to coil 30 is transferred inductively to a secondary coil 31 mounted on cage 6 and to the components in this vicinity by way of a rectifier 32.

The measurements obtained inside the antifriction bearing can be augmented by measuring the mutual radial and axial displacements of rings 1 and 2 with inductive distance sensors 33 and 34. The sensors can for example be secured to one of the rings, inner ring 2 for example, by standards 35 or straps 36, in which case they will be aimed at corresponding test areas 37 and 38 of a test ring 39 mounted on outer ring 1. The signals from these sensors are processed, as are the signals from the sensors inside the antifriction bearing, by oscillator 17, demodulator 18, amplifier 40, linearizer 41, filter 27, and signal processor 28.

We claim:

1. An arrangement for detecting and monitoring damage to races or adjacent areas on rings in roller bearings, comprising: a roller bearing with roller elements; at least one sensor positioned between said rolling elements inside said bearing and generating signals corresponding to parameters sensed; a receiver antenna outside said bearing; and means for transmitting said signals electromagnetically to said receiver antenna.

2. An arrangement as defined in claim 1, including batteries for operating said sensor and said transmitting means, said batteries being held inside said bearing.

3. An arrangement as defined in claim 1, including means outside said bearing for supplying power inductively to said sensor and said transmitting means.

4. An arrangement as defined in claim 3, including an outer ring adjacent the inside of said bearing; and an induction coil in said outer ring.

5. An arrangement as defined in claim 1, wherein said sensor comprises at least one high-frequency electromagnetic coil mounted in an area of a race exposed to wear and cracking.

6. An arrangement as defined in claim 1, wherein said sensor comprises an induction distance sensor mounted outside said rings for measuring radial bearing-play variations.

7. An arrangement as defined in claim 1, wherein said sensor comprises an induction distance sensor mounted outside said rings for measuring axial bearing-play variations.

8. An arrangement as defined in claim 1, wherein said sensor comprises an induction distance sensor mounted outside said rings for measuring radial and axial bearing-play variations.

* * * * *